US00PP20867P3

(12) United States Plant Patent
Sparks

(10) Patent No.: US PP20,867 P3
(45) Date of Patent: Mar. 23, 2010

(54) PECAN TREE NAMED 'BYRD'

(50) Latin Name: *Carya illinoinensis*
Varietal Denomination: BYRD

(75) Inventor: Darrell Sparks, Athens, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 12/220,228

(22) Filed: Jul. 23, 2008

(65) Prior Publication Data

US 2010/0024083 P1 Jan. 28, 2010

(51) Int. Cl.
*A01H 5/00* (2006.01)

(52) U.S. Cl. ..... Plt./153
(58) Field of Classification Search ..... Plt./153
See application file for complete search history.

(56) References Cited

U.S. PATENT DOCUMENTS

| | | | |
|---|---|---|---|
| PP4,236 | P | 4/1978 | Cross, Jr. |
| PP5,485 | P | 6/1985 | Clemons |
| PP5,911 | P | 3/1987 | McDowell |
| PP7,228 | P | 5/1990 | Price |
| PP7,419 | P | 1/1991 | James et al. |
| PP16,575 | P3 | 5/2006 | Clough |

*Primary Examiner*—Susan B McCormick Ewoldt
(74) *Attorney, Agent, or Firm*—Davis Wright Tremaine LLP

(57) ABSTRACT

A new and distinct cultivar of Pecan tree, *Carya illinoinensis,* which is characterized by a early nut production, early nut maturity, scab fungus resistance, and high percentage kernel.

5 Drawing Sheets

FIELD OF THE INVENTION

Figure 1:
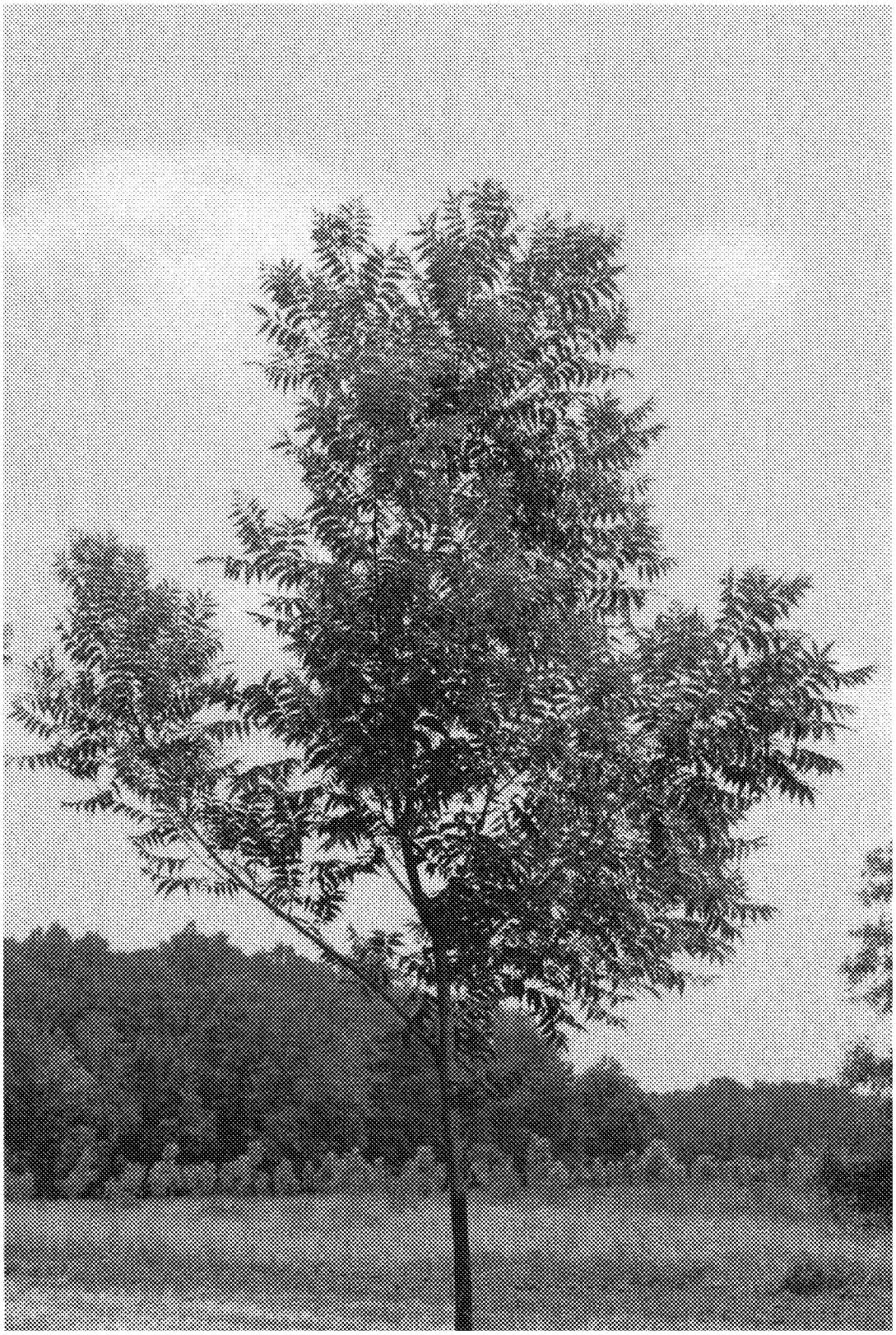

Disclosed herein is a new and distinct variety of pecan tree. Botanical classification: *Carya illinoinensis.* Varietal denomination: Pecan 'BYRD'.

BACKGROUND OF THE INVENTION

The present invention relates to a new and distinct cultivar of the nut-bearing tree *Carya illinoinensis,* known as common Pecan and hereafter referred to by the varietal denomination 'BYRD'. It can be used in gardens or for commercial production of pecan nuts.

The new pecan was selected from seedlings grown from controlled pollination on a farm in Watkinsville, Ga., in 1989. The parents of the present invention are "Pawnee" (not patented) and "Squirrel's Delight" (not patented). The seed parent was "Pawnee," while the pollen parent was "Squirrel's Delight." Graft wood of the original 'Byrd' tree has been propagated onto 28 trees in test orchards. The rootstock on which the present invention was propagated was "Elliot."

In all cases, all traits including leaf color and shape, tree form, dichogamy, flower color, fruit shape, maturity date of fruit, nut shape, kernel morphology, and percentage kernel of the nut are identical to that of the original tree.

SUMMARY OF THE INVENTION

Plants of the cultivar 'BYRD' have not been observed under all possible environmental conditions. The phenotype may vary somewhat with variations in environment such as light intensity, temperature and cultural conditions, without any variance in genotype.

The following characteristics have been consistently observed and, to the best knowledge of the inventor, their combination form the unique characteristics of 'BYRD' as a new and distinct cultivar:

1) One bract on an individual pistillate flower is two to three times longer than the other three bracts;
2) Opposite leaflets are often oriented at 180° relative to each other whereas leaflets of most pecan genotypes droop to varying degrees. The blade of apical leaflets of the leaf is undulate; and
3) Rusty-orange color blotches develop on the bark of young trees beginning about the 3rd to 4th year from planting. Shortly afterward, fissures in the bark develop within the blotches.

'BYRD' has been compared with Pecan 'Pawnee,' 'Squirrel's Delight,' 'Stuart' and 'Desirable.' 'BYRD' differed from all these varieties in the following characteristics:

1) The seed coat of the kernel does not have the commercially inferior flecking of 'Pawnee';
2) Percentage kernel (61–62) of the nut is higher than its parents, 'Pawnee' (56–57%) and 'Squirrel's Delight' (55–56%);
3) Resistance to scab [*Fusicladosporium effusum,* (G. Winters) Partridge & Morgan-Jones] is high and superior to either parent, both of which are highly susceptible to the scab fungus; 'Squirrel's Delight' is rarely grown commercially due to susceptibility to scab;
4) Nut maturity is 18–21 days before 'Stuart' and 26 days before 'Desirable', the major pecan cultivars
5) Nut maturity is similar to 'Pawnee' and 9 days before 'Squirrel's Delight'; and
6) Under humid climates, 'Byrd' is the only early nut maturing pecan cultivar with the high kernel quality needed for a diverse range of uses.

The market price for pecans is determined by the supply at any given time period and the demand during that time period. 'Byrd' matures three weeks earlier, sometimes nearly a month earlier, than other commercial varieties. 'Byrd' matures at the same time as 'Pawnee'. 'Byrd' is superior to 'Pawnee' because it has better kernel color, no flecking of kernel, and a higher percentage kernel. The price of early maturing nuts is 40 to 100% higher than that of 'Desirable' and 'Stuart'. Market price is also based on percentage kernel. Percentage kernel in 'Byrd' is higher than almost all other pecans already known and is substantially higher than all of the earliest known varieties. The nut productivity of 'Byrd' is approximately 1680 kg. per hectare. The nut can be stored, under common storage conditions for 3 months and indefinitely at 0° C. Moreover, 'Byrd' resists the major disease of pecans, scab fungus, making it more reliable for commercial investment.

Asexual reproduction by traditional grafting techniques since 2000 in Watkinsville, Albany, Leesburg, Leary, and Cordele, Ga. has shown that the unique characteristics of this new Pecan are stable and reproduced true-to-type in successive generations.

BRIEF DESCRIPTION OF PHOTOGRAPHS

FIG. 1. View of whole 'Byrd' pecan tree. Photographed May, 2008.

Figure 2:
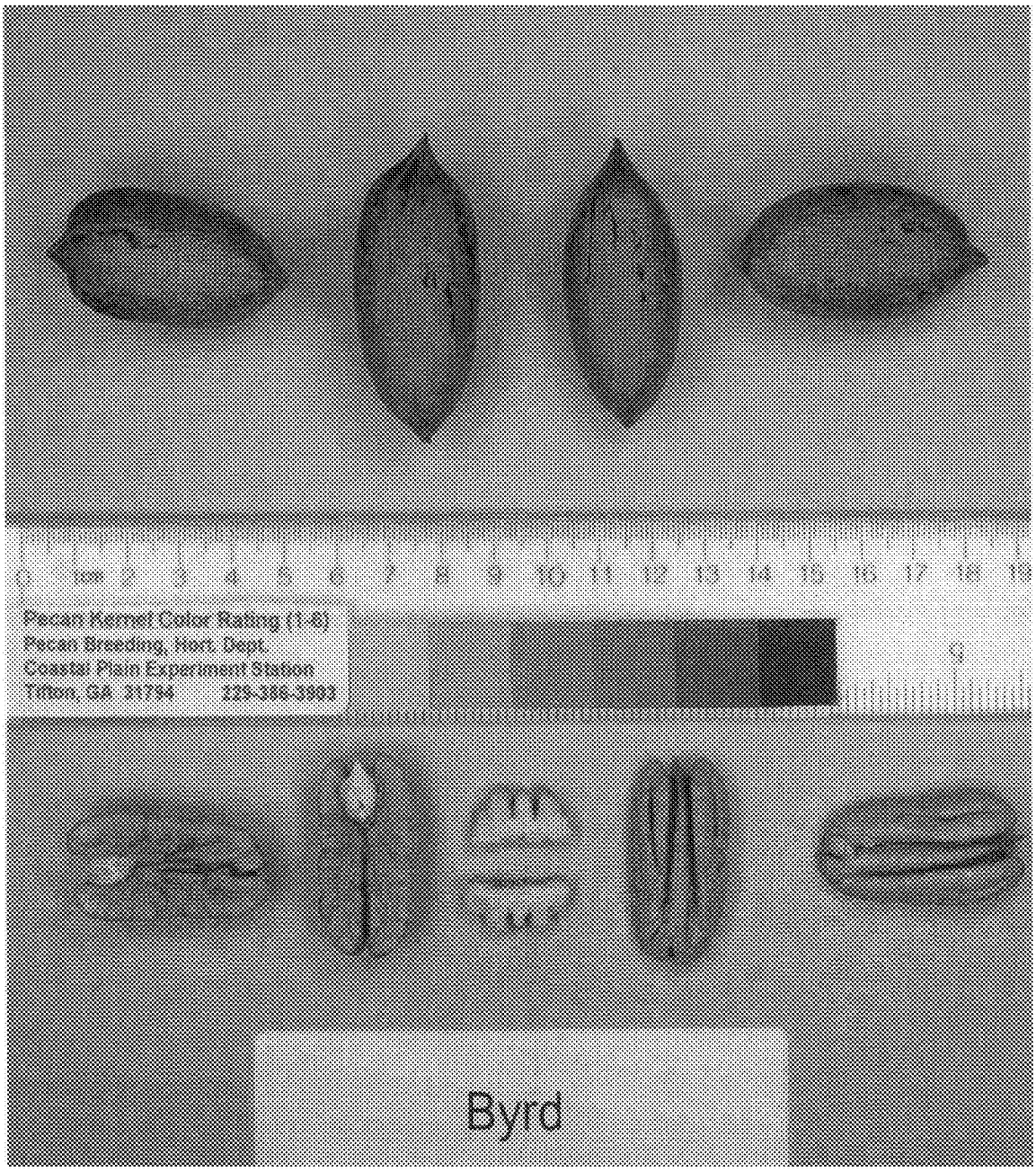

FIG. 2. Nuts (upper) and kernels (lower) of 'Byrd' pecan. Photographed in 2005. Two nuts on left were photographed on suture sides, others on non-suture sides.

Figure 3:
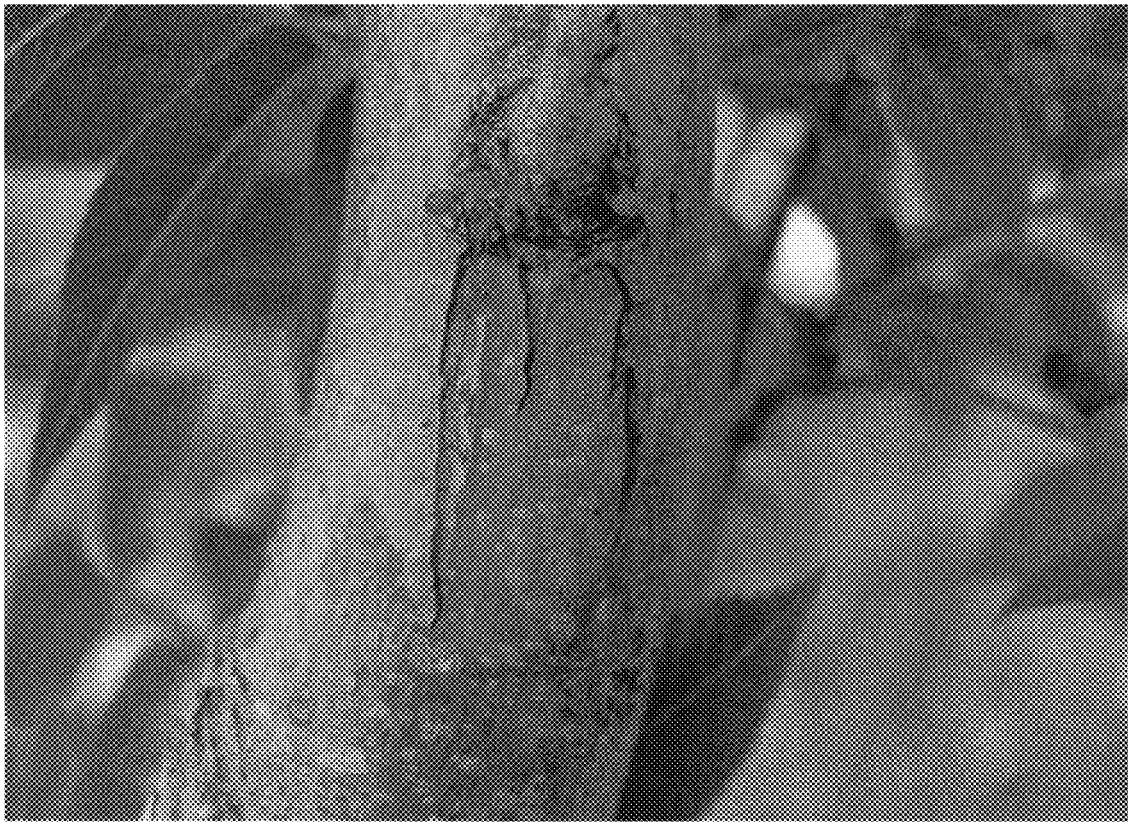

FIG. 3. Branch of 'Byrd' pecan. Rusty-orange blotch on branch of three year old tree with well-defined fissures within the blotched area. Photographed on May, 2008.

Figure 4:
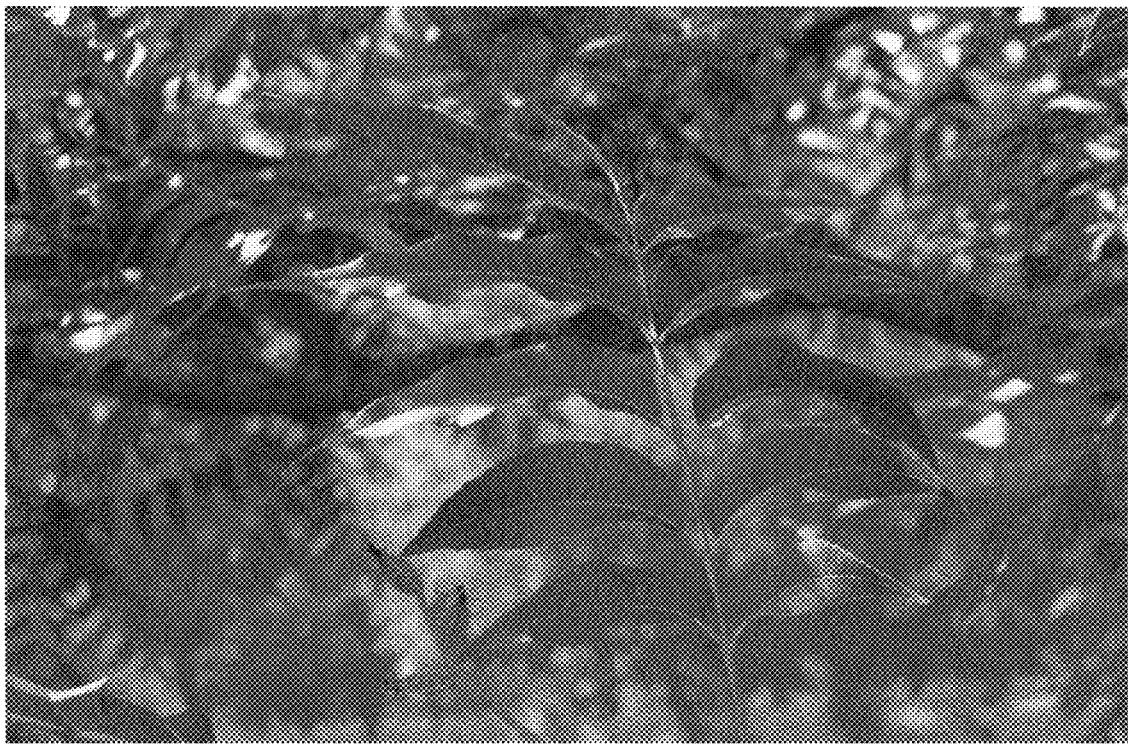

FIG. 4. Leaf of 'Byrd' pecan. Leaflets are oriented at 180 degrees, and blade of leaflet is undulated. The undulated characteristic becomes more pronounced from basal to apical leaflets of the leaf. Photographed May, 2008.

Figure 5:
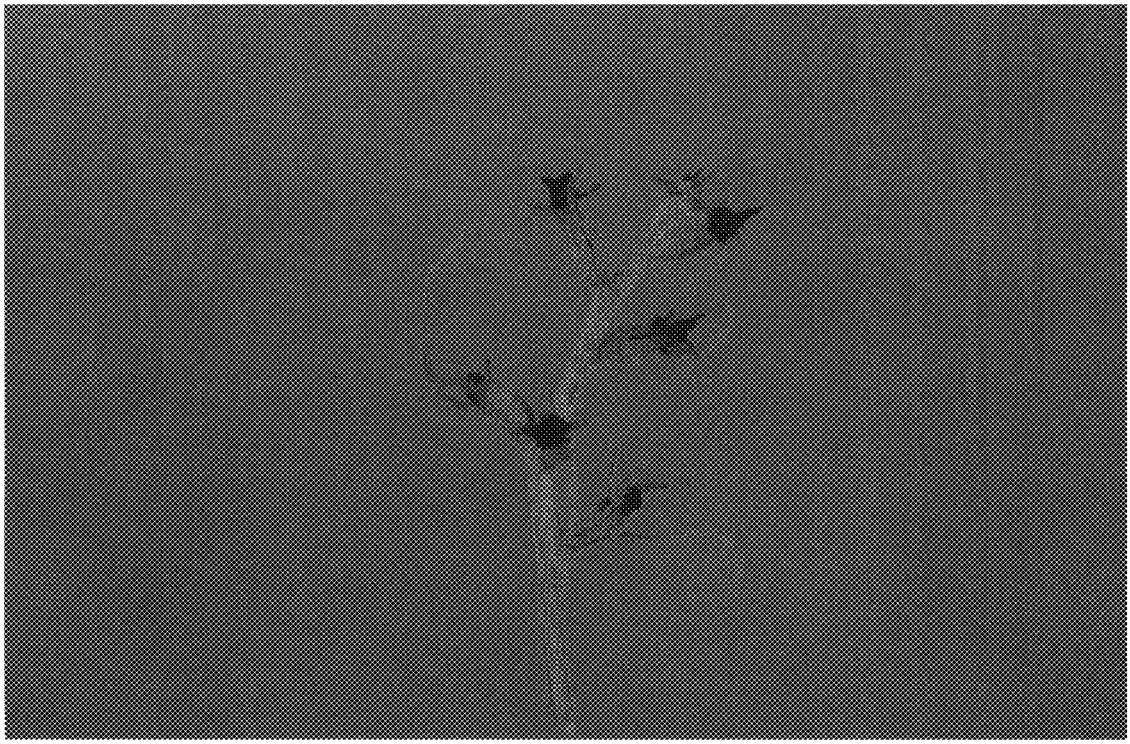

FIG. 5. Fruit cluster of 'Byrd' pecan. One bract on the more basal fruits is at least two times longer than that of the other three bracts. Photographed May, 2008.

BOTANICAL DESCRIPTION OF THE PLANT

Unless stated otherwise, the botanical description of 'BYRD' is measured data in May, 2007 on three to 18 year old trees. Observational data was from 1995–2008. The trees were grown in various locations in, Georgia (USDA Zone 7b) under conditions which closely approximate commercial production. The range of day-time growing temperatures was 65–100 degrees F. The range of night-time growing temperature was 50–75 degrees F.

Plant:

The plant is upright. Height to width ratio is about 3.0. In formulating this ratio the width was measured at the base of the canopy, which is the greatest diameter of the canopy. The base of the canopy was about 2 meters above the soil surface. The trunk diameter varies with tree age. Lenticels are present. Pecan can live up to at least 90 years and attain heights of more than 30 m. The diameter and length of the branches of the pecan tree vary with tree age.

Stems:

The stems are green in the tender stage, then brown in the woody stage. The length is 17 cm, the diameter is 5.4 mm, measured between the third and fourth leaf. The stems are round, with a tannic odor if bruised. Some rusty-orange blotches on branches with well-defined fissures within the blotched area.

Peduncle:

The peduncle is oval, green in tender stage and tan in mature stage. The fourth leaf from base is approximately 5.5 cm. The diameter of the peduncle on the fourth leaf from the base is 2.8 mm.

Leaf:

The mature leaf is odd pinnate compound, deciduous, with dark green shade on upper surface, and light green on lower surface. The average length of a mature leaf, fourth leaf from base is 39.4 cm, while the average leaf width is 20 cm. The average length of the fourth leaflet on the fourth leaf is 11.4 cm, while the average width is 3.6 cm. The leaflet apex is acuminate and narrow. The leaflet base is oblique. The leaflet margin is serrate and the shape is elliptic and falcate, with absent lobes. The leaf arrangement on a stem is alternate, with leaflet venation pinnate. The average number of leaflets on a leaf is 13.

Inflorescence:

The 'Byrd' pecan is monoecious, anemophilous and protandrous. Pistillate flowers are borne on a determinate spike, with staminate flowers borne on a determinate pendulous catkin. Six individual pistillate flowers per spike, borne alternately on terminally-positioned spikes. The pistillate flower is symmetrical with no stamens and petals. The pedicels are sessile. The staminate or catkin (average length 7.8 cm, average width 0.5 cm) is green with gold pollen. The flower has one pistil, with an oxblood color stigma. The involucre has an average length of 14.2 mm, and average width of 3.6 mm. The flower has four bracts, which are green, linear lanceolate. The bracts are on average 5.0 mm in length and 1 mm in width and are fused at the bases, forming a copular involucre.

Fruit:

The mature fruit is dehiscent.

Nut:

The weight per nut on average is approximately 9.8 g (non limiting soil moisture). The average nut length is 40 mm, while the average width is 22 mm. The nut length to width (width midway the length of the nut and across suture s) is 1.83 cm. The nut flatness (width across sutures to width between sutures) is 1.04 cm. The nut shape is oblong to slightly obovate, with a nut cross section shape being round. The nut base shape is obtuse and the nut apex is cuspidate to cuspidate asymmetric, with a grooved apex. The shell has ridges and the suture side is non elevated. The shell topography is generally rough. The observed dates of first and last pick were September 18$^{th}$ through September 30$^{th}$, respectively, in Watkinsville, Ga.

The following are color descriptions of 'Byrd,' referencing The Royal Horticultural Society (R.H.S.) Colour Chart.

Trunk: (3 to 5 year old) RHS 163A (rusty-orange)
Trunk:(mature tree) RHS 202C (black)
Winter buds: RHS 166A (greyed-orange)
Shoot:(tender stage) RHS 138B (green)
Shoot:.(woody stage) RHS 199B (brown)
Lenticels: RHS 199D (greyed-brown)
Peduncle:(tender stage) RHS 138 (green)
Peduncle:(mature stage) RHS 199B (tan)
Foliage:(upper surface) RHS 139A (dark green)
Foliage:(lower surface) RHS 138A (light green)
Pollen: RHS 3A (gold)
Stigma:RHS 61A (oxblood)
Involucre: RHS 144A (green)
Bracts: RHS 144A (green)
RHS 165A (beech brown)
Seed coat: RHS 161B (greyed-yellow)

The winter buds of 'Byrd' are about 6.3 mm long and 3.4 mm in width.

What is claimed is:

1. A new and distinct variety of pecan tree named 'BYRD', substantially as herein described and illustrated.

* * * * *

UNITED STATES PATENT AND TRADEMARK OFFICE

CERTIFICATE OF CORRECTION

PATENT NO. : PP 20,867 P3
APPLICATION NO. : 12/220228
DATED : March 23, 2010
INVENTOR(S) : Darrell Sparks It is certified that error appears in the above-identified patent and that said Letters Patent is hereby corrected as shown below:

Column 1, line 17; delete "Squirrel's Delight" and insert --Wichita--.
Column 1, line 18; delete "Pawnee" and insert --Wichita--.
Column 1, lines 18-19; delete "Squirrel's Delight" and insert --Pawnee--.
Column 2, lines 11-12, 17 and 27; delete "Squirrel's Delight" and insert --Wichita--.
Column 2, line 18; delete "55-56" and insert --58-60--.
Column 2, lines 22-23; delete "'Squirrel's Delight' is rarely grown commercially due to susceptibility to scab;".

Signed and Sealed this

Eighteenth Day of May, 2010

David J. Kappos

David J. Kappos
*Director of the United States Patent and Trademark Office*